United States Patent
Meybeck et al.

Patent Number: 5,952,001
Date of Patent: Sep. 14, 1999

[54] USE OF AN α-TOCOPHEROL PHOSPHATE OR A DERIVATIVE THEREOF FOR PREPARING COSMETIC, DERMATOLOGICAL OR PHARMACEUTICAL COMPOSITIONS, AND COMPOSITIONS THEREBY OBTAINED

[75] Inventors: Alain Meybeck; Frederic Bonte, both of Courbevoie; Christian Marechal, Paris, all of France

[73] Assignee: LVMH Recherche, France

[21] Appl. No.: 08/456,665

[22] Filed: May 30, 1995

Related U.S. Application Data

[62] Division of application No. 08/328,041, Oct. 24, 1994, Pat. No. 5,656,618, which is a division of application No. 07/917,142, filed as application No. PCT/FR91/00055, Jan. 30, 1991, Pat. No. 5,387,579.

[30] Foreign Application Priority Data

Jan. 31, 1990 [FR] France ................... 90 01143

[51] Int. Cl.⁶ .................................................. A61K 31/355
[52] U.S. Cl. ........................................... 424/450; 514/100
[58] Field of Search ............................... 514/100; 424/450

[56] References Cited

U.S. PATENT DOCUMENTS

| | | | |
|---|---|---|---|
| 4,144,325 | 3/1979 | Voyt | 424/59 |
| 4,564,686 | 1/1986 | Ogata | 549/220 |
| 4,914,197 | 4/1990 | Yamamoto et al. | 536/117 |
| 5,100,654 | 3/1992 | Pawelek et al. | 424/59 |
| 5,198,432 | 3/1993 | Fariss | 514/182 |
| 5,387,579 | 2/1995 | Meybeck et al. | 514/100 |
| 5,516,788 | 5/1996 | Sainsbury et al. | 514/410 |
| 5,643,597 | 7/1997 | Meybeck et al. | 424/450 |
| 5,652,274 | 7/1997 | Martin | 514/724 |

FOREIGN PATENT DOCUMENTS 2679904  5/1993  France .

OTHER PUBLICATIONS

WPIDS AN 91–252, 421 (Bonte et al.).

*Primary Examiner*—Jeffrey Mullis
*Attorney, Agent, or Firm*—Ostrolenk, Faber, Gerb & Soffen, LLP

[57] ABSTRACT

The present invention relates to the use of an α-tocopherol phosphate, especially in its dl or d form, or an ester thereof, of the general formula

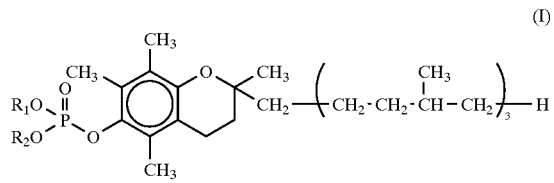

(I)

in which: $R_1$ is a hydrogen atom, an alkyl radical having from 1 to 4 carbon atoms, such as the methyl or ethyl radical in particular, or an α-tocopheryl radical; and $R_2$ is a hydrogen atom, an alkyl radical having from 1 to 4 carbon atoms, such as methyl or ethyl radical in particular, or an oxyethylene chain of the formula

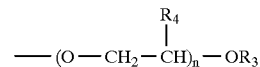

in which $R_3$ and $R_4$ independently are a hydrogen atom or a methyl radical and n is an integer greater than or equal to 1, or a salt thereof, for preparing a pharmaceutical, dermatological or cosmetic composition for the prevention or treatment of allergic manifestations such as skin allergy or bronchial asthma, or inflammatory manifestations, or for the prevention or treatment of the harmful effects of free radicals.

20 Claims, No Drawings

USE OF AN α-TOCOPHEROL PHOSPHATE OR A DERIVATIVE THEREOF FOR PREPARING COSMETIC, DERMATOLOGICAL OR PHARMACEUTICAL COMPOSITIONS, AND COMPOSITIONS THEREBY OBTAINED

This is a division of application Ser. No. 08/328,041, filed Oct. 24, 1994, now U.S. Pat. No. 5,656,618, which is a division of application Ser. No. 07/917,142, filed under 35 USC 371, filed Jul. 31, 1992, now U.S. Pat. No. 5,387,579, which is the national stage filing of PCT/FR91/00055, filed Jan. 30, 1991, which corresponds to French patent application number 90/01143, filed Jan. 31, 1990. Foreign priority of Jan. 31, 1990, is claimed.

The present invention relates in general terms to the use of an α-tocopherol phosphate, or an ester thereof, or a salt of these compounds, for preparing pharmaceutical, cosmetic or dermatological compositions with antiallergic or antiinflammatory activity or for the prevention or treatment of the harmful effects of free radicals, and to pharmaceutical, cosmetic or dermatological compositions with antiallergic or antiinflammatory activity or for the prevention or treatment of the harmful effects of free radicals, in which said compound is incorporated.

It is known that vitamin E has the common name of α-tocopherol in particular (see Merck Index, 10th edition, reference 9832, page 1437).

α-Tocopherol occurs in the natural state in numerous plants, usually with other compounds such as β-tocopherol and γ-tocopherol.

It is also known that α-tocopherol exists in both the dl and d forms.

α-Tocopherol is essentially used for controlling vitamin E deficiencies or as a nutritional factor, especially for controlling muscle degeneration.

It is also used as an antioxidant, but at very specific doses.

α-Tocopherol esters have also been described, in particular the succinate, the nicotinate or the acetate (Merck Index, 10th edition, references 9832, 9833, page 1437). The synthesis of α-tocopherol acetate is also described in U.S. Pat. No. 2,723,278 and that of other esters is described in the document J. Amer. Chem. Soc. (1943) 65, 918–924.

dl-α-Tocopherol phosphate is also known (see P. KARRER et al., Helv. Chim. Acta (1940) 23, 1137–8), as is its action on muscle metabolism (see J. Biol. Chem. 1942, 146, pages 309–321). Another document describes the biological role as an antioxidant on brain tissue (Biol. Antioxidants Trans., 1st Conf., 1946, pages 61–62). An anticoagulant action through an action on the polymerization of fibrin has also been described (Can. J. Biochem. and Physiol. 1959, 37, pages 501–505). An antimicrobial action in vitro on *B. subtilis* and *S. aureus* has also been described (Naturwissenschaften 1960, 47, page 17).

In another connection, German patent application A-3 416 209 describes the use of creams containing vitamin E for the treatment and prevention of inflammatory processes. By contrast, Berkenkopf and Lutsky have described that the injection of vitamin E into rats causes a chronic localized inflammation (Agents Actions 1979, 9, (4), 350–357).

Thus the action of vitamin E on inflammation is controversial.

It has now been discovered, totally surprisingly and unexpectedly, that α-tocopherol phosphate, especially in its dl or d form, or an ester thereof, of the general formula

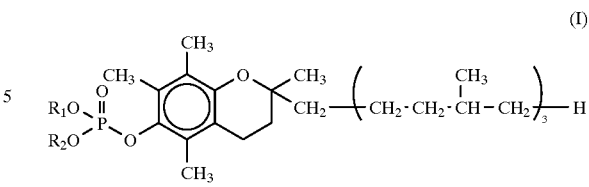

in which:

R$_1$ is a hydrogen atom, an alkyl radical having from 1 to 4 carbon atoms, such as the methyl or ethyl radical in particular, or an α-tocopheryl radical; and R$_2$ is a hydrogen atom or an alkyl radical having from 1 to 4 carbon atoms, such as a methyl or ethyl radical in particular, or R$_2$O is an oxyethylene chain of the formula

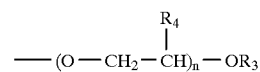

in which R$_3$ and R$_4$ independently are a hydrogen atom or a methyl radical and n is an integer greater than or equal to 1, or a salt thereof, can be used for preparing a pharmaceutical, dermatological or cosmetic composition for the prevention or treatment of allergic manifestations such as skin allergy or bronchial asthma, or inflammatory manifestations, or else for the prevention or treatment of the harmful effects of free radicals.

Thus the object of the present invention is to solve the new technical problem which consists in providing an active substance having a good antiallergic activity, especially for the prevention or treatment of skin allergy or bronchial asthma, or a good antiinflammatory activity, or else a preventive or curative activity against the harmful effects of free radicals, in particular by topical or general administration, thereby constituting a valuable active ingredient for preparing cosmetic, dermatological or pharmaceutical compositions.

The present invention solves this new technical problem satisfactorily with a particularly simple solution which can be used on the industrial scale.

Thus, according to a first feature, the present invention covers the use of an α-tocopherol phosphate, especially in its dl or d form, or an ester thereof, of the general formula

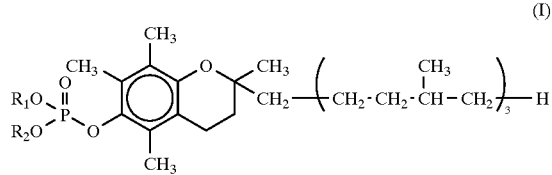

in which:

R$_1$ is a hydrogen atom, an alkyl radical having from 1 to 4 carbon atoms, such as the methyl or ethyl radical in particular, or an α-tocopheryl radical; and R$_2$ is a hydrogen atom or an alkyl radical having from 1 to 4 carbon atoms, such as a methyl or ethyl radical in particular, or R$_2$O is an oxyethylene chain of the formula

in which $R_3$ and $R_4$ independently are a hydrogen atom or a methyl radical and n is an integer greater than or equal to 1, or a salt thereof, for preparing a pharmaceutical, dermatological or cosmetic composition for the prevention or treatment of allergic manifestations such as skin allergy or bronchial asthma, or inflammatory manifestations, or for the prevention or treatment of the harmful effects of free radicals.

Thus the products used according to the present invention are α-tocopherol phosphates or esters thereof, it being possible for these products to take the form of cosmetically, dermatologically or pharmaceutically acceptable salts such as, for example, alkali metal salts, especially sodium salts (monosodium or disodium salt), or alkaline earth metal salts, especially magnesium salts, or else ammonium salts or salts of primary, secondary or tertiary amines such as, in particular, diethylamine, diethanolamine, triethylamine or triethanolamine.

In formula (I) the alkyl radicals can have a linear or branched chain.

An alkyl radical having from 1 to 4 carbon atoms is for example methyl, ethyl, propyl, isopropyl or butyl, preferably methyl or ethyl.

α-Tocopheryl radical is understood as denoting the radical

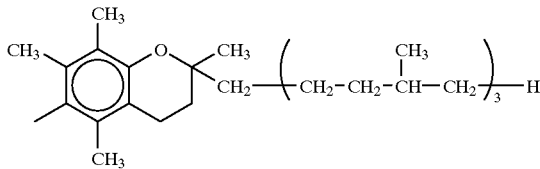

When $R_2O$ is an oxyethylene chain, n will generally be greater than or equal to 1, for example between 2 and 50, preferably between 2 and 25 and in particular equal to 2 or 5.

In another advantageous embodiment according to the invention, a compound of formula I as defined above, preferably as a salt, is used in the form of small liposome-type vesicles obtained by dispersing said compound or said salt in water or in an aqueous medium such as a buffer solution, especially by means of mechanical stirring followed by homogenization, for example with the aid of ultrasound or a homogenizer under pressure.

Preferably, the size of these vesicles is adjusted to a value of between about $6 \times 10^{-2}$ μm and 2 μm by modifying the homogenization parameters such as the energy and the duration.

In an advantageous variant of the previous embodiment, the above-mentioned aqueous medium contains a biologically active agent, said agent being at least partially encapsulated after dispersion in the above-mentioned vesicles.

Preferably, the above-mentioned active agent is an antiallergic substance such as an extract of Scutellaria, for example an extract of the root of *Scutellaria baicalensis* Georgi described in French patent application A-2 628 317, or an antiinflammatory substance.

In an advantageous embodiment of the use according to the invention, the concentration by weight of the compound of formula (I) mentioned above, or a salt thereof, is between 0.001 and 10%, preferably between 0.01% and 1% and particularly preferably between 0.05 and 0.5%, relative to the total weight of the composition.

In a currently preferred embodiment, the compound of formula (I) mentioned above is dl-α-tocopherol phosphate. The preferred salts are the monosodium salts and the disodium salt.

The compounds used according to the invention are generally commercially available and can be prepared especially by following procedures described in the literature, for example in Chem. Pharm. Bull. (1971) 19, (4), pages 687 to 695; Khim.-Pharm. Zh. (1983) 17, (7), pages 840 to 844; Khim.-Pharm. Zh. (1985) 19, (1), pages 75 to 77, or else in U.S. Pat. No. 2,457,932 or Japanese patent 54-54 978.

According to a second feature, the present invention covers a cosmetic or dermatological composition which comprises, as the active ingredient, at least one compound of formula (I) or a salt thereof, as defined above.

In an advantageous embodiment, the cosmetic or dermatological composition comprises, as the active ingredient, at least one compound of formula (I) as defined above, preferably as a salt, in the form of small liposome-type vesicles obtained by dispersing said compound or said salt in water or in an aqueous medium such as a buffer solution, especially by means of mechanical stirring followed by homogenization, for example with the aid of ultrasound or a homogenizer under pressure.

Preferably, the size of these vesicles is adjusted to a value of between about $6.10^{-2}$ μm and 2 μm by modifying the homogenization parameters such as the energy and the duration.

In an advantageous variant of the previous embodiment, the above-mentioned aqueous medium contains a biologically active agent, said agent being at least partially encapsulated after dispersion in the above-mentioned vesicles.

Preferably, the above-mentioned active agent is an antiallergic substance such as an extract of Scutellaria, for example an extract of the root of *Scutellaria baicalensis* Georgi described in French patent application A-2 628 317, or an antiinflammatory substance.

In another advantageous embodiment, said cosmetic or dermatological compositions are prepared for the prevention and treatment of allergic manifestations such as skin allergy or bronchial asthma, or inflammatory manifestations, or for the prevention or treatment of the harmful effects of free radicals.

The concentration of active ingredients in these cosmetic or dermatological compositions is as described above for their use.

The compositions according to the invention can be formulated in any form acceptable for their use in cosmetology, dermatology or pharmacy. In particular, they can be in the form of a preventive and curative skin allergy cream, a soothing antiallergic cream, a soothing antiallergic oil, a preventive or curative antiallergic lotion, an alcoholic aftershave lotion for soothing skin irritations, a hypoallergenic cream or a colloidal antiasthmatic solution, or else in the form of a solution for controlling the toxic effects of the superoxide radicals which are formed as a result of intensive care techniques using oxygen.

The compositions according to the invention can also be formulated as make-up compositions such as make-up foundation, lipstick, mascara and pigmented powder.

According to a third feature, the present invention covers a method of reducing the allergic or irritant potential of a pharmaceutical, dermatological or cosmetic composition, which consists in incorporating into said composition an effective amount of at least one compound of formula (I) or at least one salt thereof, as defined above.

In a currently preferred embodiment, the compound of formula (I) mentioned above is dl-α-tocopherol phosphate. The preferred salts are the monosodium salts and the disodium salt.

Advantageously, the concentration of compound of formula (I) or salt thereof is as described above for its use.

According to a fourth feature, the present invention further relates to a process for the manufacture of a cosmetic or dermatological composition intended in particular for the prevention or treatment of allergic manifestations such as skin allergy, or inflammatory manifestations, or for the prevention or treatment of the harmful effects of free radicals, which comprises incorporating a compound of formula (I) or a salt thereof, as defined above, into a cosmetically or dermatologically acceptable excipient, vehicle or carrier.

According to a fifth feature, the present invention further covers a process for the manufacture of a pharmaceutical composition for the prevention or treatment of allergic manifestations such as bronchial asthma, or inflammatory manifestations, or for the prevention or treatment of the harmful effects of free radicals, which comprises incorporating a compound of formula (I) or a salt thereof, as defined above, into a pharmaceutically acceptable excipient, vehicle or carrier.

The incorporation of the compound of formula I or a salt thereof into said cosmetic, dermatological or pharmaceutical composition can be effected by different methods accessible to those skilled in the art, depending on the desired type of formulation.

In an advantageous mode of carrying out said manufacturing processes, when the composition comprises an aqueous phase, the compound of formula (I) mentioned above is first dispersed, preferably in the form of a salt as already defined, in water or in said aqueous phase to form small vesicles, and the resulting dispersion is then mixed with the other possible constituents of the composition.

According to a sixth feature, the present invention covers a method of preventing or treating allergic manifestations such as skin allergy or bronchial asthma, or inflammatory manifestations, or of preventing or treating the harmful effects of free radicals, which comprises applying an effective amount of at least one compound of formula (I) or a salt thereof, as defined above, incorporated in a cosmetically, dermatologically or pharmaceutically acceptable excipient, vehicle or carrier.

The invention will now be illustrated in detail with the aid of several practical Examples, which are given simply by way of illustration and cannot in any way limit the scope of the invention.

Unless indicated otherwise, the percentages are given by weight in the Examples.

EXAMPLE 1 a) Preparation of a suspension of monosodium dl-α-tocopherol phosphate 0.8 g of powdered disodium dl-α-tocopherol phosphate, obtained by the method described by P. KARRER (Helv. Chim. Acta (1940) 23, 1137–8), is weighed out.

This powder is poured into 96.2 g of double-distilled water, with stirring, and stirring is continued for about 2 hours.

The mixture is then homogenized by ultrasound for 10 min at 150 W until a clear suspension is obtained, which gives rise to the production of liposome-type vesicles of disodium tocopherol phosphate.

Where larger volumes are involved, a homogenizer under pressure can advantageously be used, for example a homogenizer of the Manton-Gaulin® type at a pressure of about 500 bar.

The pH is subsequently lowered to 7 by the addition of about 3 ml of 0.5 N HCl, with stirring, and then adjusted to 6.5 by the addition of 0.1 N HCl, with stirring. At this pH the tocopherol phosphate is now in the form of the monosodium salt.

The resulting size of the vesicles of monosodium α-tocopherol phosphate can be determined for example by means of an Autosizer 2C from MALVERN. The average size measured in this Example is of the order of 100 nm.

It will also be noted that various dilutions can be made by modifying the amount of compounds added at the start or by modifying the volume of the dispersion solution, which represents an easy method of preparing various concentrations of active principle.

The Example described gave about 100 g of suspension containing about 0.8% of monosodium dl-α-tocopherol phosphate in the form of liposome-type vesicles of substantially homogeneous sizes.

b) Preparation of a gelled composition of monosodium α-tocopherol phosphate

The homogenized suspension obtained above can be gelled by mixing with a gel such as a vinylic polymer gel, in particular the one marketed under the tradename Carbopol® 940.

In a manner known per se, this gel can be prepared for example by dispersing 1 g of Carbopol® 940 in 99 g of water in the presence of a preservative, and then, after swelling, by neutralizing to pH 7.5, for example with triethanolamine.

100 g of this gel are added to the 100 g of homogenized suspension obtained above to give a gelled composition having a monosodium α-tocopherol phosphate concentration of about 0.4%.

Gelled compositions having various α-tocopherol phosphate concentrations can be obtained by the method indicated above.

EXAMPLE 2

Demonstration of the antiallergic activity and antifree radical activity of the compositions according to the invention A. Antiallergic Activity The purpose of this study is to demonstrate antiallergic effects on the skin after sensitization with DNFB (2,4-dinitro-1-fluorobenzene).

a) Experimental protocol 64 female BalB/C mice, having essentially the same weight and showing no detectable signs of allergy, are divided up into eight groups of eight animals.

Group no. 1 receives only DNFB.

Group no. 2 receives only isotonic solution and a nonirritant dose of DNFB.

Groups no. 3 to 8 receive a test product after sensitization with DNFB, the test products being respectively as follows:

Group no. 3: gel of monosodium dl-α-tocopherol phosphate (TP.Na) according to the invention Group no. 4: gel of dl-α-tocopherol (α-toco)

Group no. 5: gel of dl-α-tocopherol acetate (Ac-toco)

Group no. 6: gel of polyethoxylated d-α-tocopherol succinate (Vit. E TPGS)

Group no. 7: gelled excipient of α-toco and Ac-toco (T1)

Group no. 8: gelled excipient of TP.Na and Vit. E. TPGS (T2)

The procedure is more precisely as follows:
1) Preparation of the test products

The concentration of each substance is determined so that the test products are equimolar in respect of tocopherol.

a) Gel containing 0.128% of monosodium dl-α-tocopherol phosphate (TP.Na) according to the invention This gel is prepared as indicated in Example 1.

b) Gel containing 0.1% of dl-α-tocopherol (α-toco)

0.1 g of α-toco is dissolved in 49.9 g of absolute ethanol. The solution is stirred at room temperature and then mixed with 50 g of Carbopol® 940 gel.

c) Gel containing 0.109% of dl-α-tocopherol acetate (Ac-toco)

0.109 g of Ac-toco is dissolved in 49.891 g of absolute ethanol and the solution is then mixed with 50 g of Carbopol® 940 gel.

d) Gel containing 0.357% of Vit. E TPGS (polyethylene glycol 1000 d-α-tocopherol succinate)

0.357 g of Vit. E TPGS is dissolved in 49.643 g of double-distilled water. The solution is heated at 70° C., with stirring, until dissolution is complete (about 15 min). It is left to return to room temperature (the solution remains clear). 50 g of Carbopol® 940 gel are then added.

e) Gelled excipient of α-toco and Ac-toco (T1)

This excipient is a 50/50 mixture of absolute ethanol and Carbopol® 940 gel.

f) Gelled excipient of TP.Na and Vit. E TPGS (T2)

This excipient is a 50/50 mixture of double-distilled water and Carbopol® 940 gel.

2) Sensitization with DNFB

On day D-0 groups 1 and 3 to 8 receive, by injection into a paw, a sensitizing dose of 55 µl of a 1% solution of DNFB in absolute ethanol, diluted two-fold with Freund's adjuvant.

Group no. 2 receives isotonic solution under the same conditions.

3) Application of the products

From day D-1 to day D-7 groups no. 3 to 8 receive a daily application of 100 µl of test product deposited on the inside of the right ear and then spread delicately over both sides of the ear with the aid of a syringe.

On day D-7 this application is made 1 h 30 min after the initiating administration of DNFB described below.

4) Initiating administration of DNFB

On day D-7 groups 1 to 8 receive, on both sides of the right ear, a non-irritant initiating dose of 100 µl of a 0.1% solution of DNFB in absolute ethanol.

5) Development of the antiallergic effect 24 hours after the initiating application of DNFB, the animals are sacrificed and the right ears are delicately removed and then weighed.

b) Results The results obtained have been reported in Table I below.

This Table contains the mean weight (M) of the right ears for each group, the standard deviation (e) of M and the percentage protection (P) against the action of DNFB.

The percentage protection P was calculated using the formula $$P = \frac{M_1 - M_P}{M_1 - M_2} \times 100$$

in which $M_1$ is the mean weight for group 1 (DNFB), $M_2$ is the mean weight for group 2 (isotonic solution), and $M_P$ is the mean weight for groups 3 to 8 (test products).

The comparison of the results was evaluated statistically by means of the Student test:

($S_1$): between groups 3 to 8 and group 1 (DNFB—positive control)

($S_2$): between groups 3 to 8 and group 2 (isotonic solution—negative control).

TABLE I

|  | M | e | P % | $S_1$ | $S_2$ |
|---|---|---|---|---|---|
| Group 1 (DNFB) | 161.7 | 12.4 |  |  |  |
| Group 2 (iso. sol.) | 133.7 | 9.6 |  |  |  |
| Group 3 (TP.Na) | 144.0 | 16.4 | +63.2 | s | ns |
| Group 4 (α-toco) | 173.5 | 18.8 | −42.1 | ns | s |
| Group 5 (Ac-toco) | 161.8 | 12.5 | −0.3 | ns | s |
| Group 6 (Vit. E TPGS) | 161.8 | 7.7 | −0.3 | ns | s |
| Group 7 (T1) | 159.8 | 18.2 | +6.7 | ns | s |
| Group 8 (T2) | 152.7 | 19.9 | +32.1 | ns | s | s : significant
ns: not significant

It can be seen from Table I that the edema caused by the action of DNFB is significantly reduced by the product according to the invention (TP.Na), whereas in this model the comparative products, in particular dl-α-tocopherol and dl-α-tocopherol acetate, have no influence or have even increased the reaction caused by DNFB.

The antiallergic activity of the compounds according to the invention is therefore particularly high and surprising, especially in view of the negative activity of tocopherol.

Various Examples of topical, dermatocosmetic or pharmaceutical compositions, especially dermatological compositions, are given below.

B. Study of the anti-free radical activity

This study is performed according to the protocol described by M. S. NOEL-HUDSON, C. de BELILOVSKI, N. PETIT, A. LINDENBAUM, J. WEPIERRE in TOXIC. in vitro, 1989, 3, (2), 103–109.

Tests are carried out on cultures of human keratinocytes. The stock solution of the test product according to the invention is a 0.1% aqueous solution of disodium d-α-tocopherol phosphate. This solution is used at different dilutions in MCDB153 culture medium (Irvine®) supplemented with ethanolamine, phosphoethanolamine, cortisone, insulin and calcium (0.1 mM), so as to give the following concentrations of d-α-tocopherol phosphate salt: $10^{-3}\%$, $5.10^{-4}\%$, $10^{-4}\%$ and $5.10^{-5}\%$.

The test dilution is brought into contact with the culture cells for 48 hours just after inoculation.

The culture medium is then discarded and the cells are rinsed with phosphate buffer. The hypoxanthine/xanthine oxidase system (HX-XO), which is a free radical generator, is then applied for 2 hours 30 minutes. After a further rinse with phosphate buffer, the cytotoxicity is determined by the so-called neutral red method (Borenfreund and Puerner, 1985).

The values shown in Table II represent the cell viability expressed as the percentage of living cells relative to the total number of cells in the culture in question.

TABLE II

| | Concentrations of the test product | | | | |
|---|---|---|---|---|---|
| | 0% | $10^{-3}\%$ | $5.10^{-4}\%$ | $10^{-4}\%$ | $5.10^{-5}\%$ |
| Control cultures | 100 | 66.40 | 87.92 | 94.28 | 100 |
| Treated cultures (HX—XO) | 10.57 | 39.59 | 32.79 | 12.19 | 9.28 |

It is seen that the percentage cell viability is very considerably improved in the cultures which have been in contact with the product according to the invention prior to treatment with the HX-XO system, compared with that of the culture to which no product has been added beforehand.

This very clearly shows the preventive protective activity of the product according to the invention against the cytotoxic action of free radicals such as those produced by the hypoxanthine/xanthine oxidase system.

Examples of Pharmaceutical or Cosmetic Formulations Containing Vitamin E Phosphate

EXAMPLE 3

Preventive and curative skin allergy cream

| Composition: | | |
|---|---|---|
| A | Cera bellina | 5.00 g |
| | Silicone 200 | 1.50 g |
| | Squalane | 5.00 g |
| | Myglyol 812 | 5.00 g |
| | Nylon 12 SP 500 | 3.00 g |
| | BHT | 0.05 g |
| B | Demineralized water | 49.56 g |
| | EDTA | 0.10 g |
| | Propylene glycol | 4.00 g |
| | Carbopol ® 1342 | 0.45 g |
| | Triethanolamine | 0.54 g |
| | 0.4% dispersion of monosodium dl-α-tocopherol phosphate, pH 6.6 | 25.00 g |
| C | Germaben II ® | 0.80 g |

Procedure: Mixture A is heated, with stirring, to give a homogeneous mixture. Mixture B is prepared by dispersing the Carbopol® 1342 in an aqueous solution containing the EDTA and the propylene glycol in 49.56 g of distilled water, and neutralizing with the triethanolamine. The 0.4% dispersion (non-gelled) of dl-α-tocopherol phosphate, obtained according to Example 1, is then added.

Mixture B is then heated to 75° C. and held at this temperature, with stirring, while mixture A is added. The resulting mixture is left to cool to 45° C., the Germaben II® is then added and the mixture is left to cool further to room temperature, with stirring.

This gives a cream.

EXAMPLE 4

Soothing antiallergic cream

| Composition: | | |
|---|---|---|
| A | Soya lecithin | 2.00 g |
| | Cosbiol ® | 8.50 g |
| B | Demineralized water | 58.85 g |
| | EDTA | 0.10 g |
| | Glycerol | 4.00 g |
| | Carbopol ® 940 | 0.35 g |
| | Triethanolamine | 0.40 g |
| | Germaben II ® | 0.80 g |
| C | 0.4% dispersion of monosodium α-tocopherol phosphate, pH 6.6 | 25.00 g |

Procedure: The Cosbiol® and the lecithin are heated, with stirring, until they have completely dissolved, and the solution is left to cool to room temperature. Mixture B is obtained by dispersing the Carbopol® 940 in the mixture water +EDTA +glycerol. The whole is neutralized with the triethanolamine, after which the Germaben II® is added.

Mixture A is then poured into mixture B, with stirring. The resulting mixture is homogenized and the dispersion obtained as in Example 1 is then added. The mixture is homogenized again to give a cream which can be applied locally in the morning and evening to soothe allergic skin reactions.

EXAMPLE 5

Soothing antiallergic oil 0.1 g of powdered disodium α-tocopherol phosphate is dissolved in 99.9 g of trioctyl citrate at 70° C. for 8 h, with magnetic stirring.

The resulting oily solution can be applied locally, like the cream of Example 4.

EXAMPLE 6

Alcoholic aftershave lotion

| Composition: | |
|---|---|
| Disodium α-tocopherol phosphate | 0.2 g |
| Ethanol | 40 g |
| Propylene glycol | 0.5 g |
| Pantothenol | 0.1 g |
| Perfumed aqueous excipient qsp | 100 g |

Preparation: The disodium tocopherol phosphate is dissolved in the absolute alcohol, and the other constituents are dissolved in the water to give a separate solution. The two solutions obtained are mixed and the whole is homogenized by means of ultrasound.

This lotion makes it possible to soothe the irritations due to shaving, which are commonly referred to as "smarting".

EXAMPLE 7

Preventive or curative antiallergic lotion

| Composition: | |
|---|---|
| 4% dispersion of monosodium α-tocopherol phosphate | 25.00 g |
| Ethanol | 10.00 g |
| Propylene glycol | 5.00 g |
| Aqueous excipient qsp | 100.00 g |

The 4% dispersion of α-tocopherol phosphate is prepared as in Example 1, except that this dispersion has a greater concentration of monosodium α-tocopherol phosphate.

The constituents of the above formulation are mixed together and homogenized by means of ultrasound.

EXAMPLE 8

Colloidal antiasthmatic solution

| Composition: | |
|---|---|
| 4% dispersion of monosodium α-tocopherol phosphate | 12.50 g |
| Buffered aqueous excipient + preservative qsp | 100.00 g |

The dispersion of monosodium tocopherol phosphate is prepared as in Example 1. After homogenization with ultrasound, a colloidal solution is obtained which is then incorporated into the buffered excipient.

This solution can be used as a spray in the upper respiratory tract, especially for soothing asthmatic coughs.

EXAMPLE 9

Colloidal solution for intensive care techniques

| Composition: | |
| --- | --- |
| 4% dispersion of monosodium α-tocopherol phosphate | 7.50 g |
| Buffered aqueous excipient + preservative qsp | 100.00 g |

This composition is prepared as in the previous Example.

It can be used for controlling the toxic effects of the superoxide radicals which are formed as a result of intensive care techniques using oxygen. In this case it is administered as an intratracheal instillation at the same time as the gaseous mixture is administered.

EXAMPLE 10

Antiallergic make-up foundation

| Composition: | |
| --- | --- |
| Disodium dl-α-tocopherol phosphate | 0.5 g |
| Emulsion for make-up foundation | 99.5 g |

This composition is prepared by incorporating the disodium tocopherol phosphate, previously dispersed in water, into the aqueous phase of the emulsion. The emulsion is then prepared by the conventional procedure.

This make-up foundation minimizes the risks of allergic manifestations due to a raw material or to an allergenic substance coming into contact with the skin.

What we claim is:

1. A method for cosmetic care comprising topically applying onto any body skin area of a person a cosmetically effective amount of a tocopherol compound selected from the group consisting of:

a) an α-tocopherol compound of general formula (I), as follows:

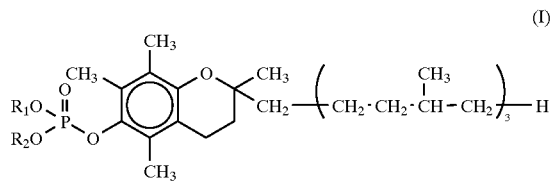

(I)

wherein:

$R_1$ represents a hydrogen atom, an alkyl radical having from 1 to 4 carbon atoms, or an alpha-tocopheryl radical, $R_2$ represents a hydrogen atom, an alkyl radical having from 1 to 4 carbon atoms, or $R_2O$ represents an oxyethylenated chain, of formula

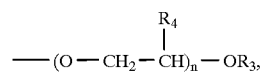

wherein $R_3$ and $R_4$ represent independently a hydrogen atom or a methyl radical, and n represents an integer number greater than or equal to 1;

b) a DL form of said tocopherol compound of formula (I);

c) a D form of said tocopherol compound of formula (I);

d) a cosmetically acceptable ester of said tocopherol compound of formula (I), wherein at least one of $R_1$ and $R_2$ is alkyl, alpha-tocopheryl, or $R_2O$ represents said oxyethylenated chain; and e) a cosmetically acceptable salt of said tocopherol compound of formula (I), said tocopherol compound being optionally incorporated in a cosmetically acceptable excipient.

2. The method of claim 1, wherein said compound of formula (I) is in a form of small liposomal vesicles obtained by dispersion of said compound in water or in an aqueous medium.

3. The method of claim 2, wherein said tocopherol compound is present in a form of a cosmetically acceptable salt.

4. The method of claim 2, wherein said vesicles range in size between $6\times10^{-2}$ micrometers and 2 micrometers.

5. The method of claim 2, wherein said vesicles contain a biologically active agent in addition to said compound of formula (I).

6. The method of claim 1, further comprising incorporating said compound of formula (I) in a cosmetically acceptable excipient to constitute a composition, said compound of formula (I) being present in a weight concentration ranging from 0.001% to 10% with respect to a total weight of said composition.

7. The method of claim 1, wherein said compound of formula (I) is DL-alpha-tocopherol phosphate.

8. The method of claim 1, wherein said salt of said compound of formula (I) is selected from a monosodium salt and a disodium salt.

9. A method for protecting skin cells from damage caused by free radicals comprising topically applying onto any body skin area of a patient an effective amount of a tocopherol compound selected from the group consisting of:

a) an alpha-tocopherol compound of general formula (I), as follows:

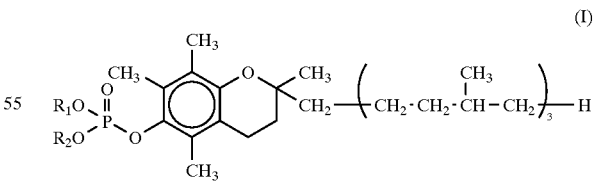

(I)

wherein:

$R_1$ represents a hydrogen atom, an alkyl radical having from 1 to 4 carbon atoms, or an alpha-tocopheryl radical, $R_2$ represents a hydrogen atom, an alkyl radical having from 1 to 4 carbon atoms, or $R_2O$ represents an oxyethylenated chain, of formula $$—(O—CH_2—\overset{R_4}{\underset{|}{CH}})_n—OR_3,$$

wherein $R_3$ and $R_4$ represent independently a hydrogen atom or a methyl radical, and n represents an integer number greater than or equal to 1;
b) a DL form of said tocopherol compound of formula (I);
c) a D form of said tocopherol compound of formula (I);
d) a cosmetically or pharmaceutically acceptable ester of said tocopherol compound of formula (I), wherein at least one of $R_1$ and $R_2$ is alkyl, alpha-tocopheryl, or $R_2O$ represents said oxyethylenated chain; and
e) a cosmetically or pharmaceutically acceptable salt of said tocopherol compound of formula (I),
said tocopherol compound being optionally incorporated in a cosmetically or pharmaceutically acceptable excipient.

10. The method of claim 9, wherein said compound of formula (I) is in a form of small liposomal vesicles obtained by dispersion of said compound in water or in an aqueous medium.

11. The method of claim 10, wherein said tocopherol compound is present in a form of a cosmetically acceptable salt.

12. The method of claim 10, wherein said vesicles range in size between $6 \times 10^{-2}$ micrometers and 2 micrometers.

13. The method of claim 10, wherein said vesicles contain a biologically active agent in addition to said compound of formula (I).

14. The method of claim 9, further comprising incorporating said compound of formula (I) in a cosmetically acceptable excipient to constitute a composition, said compound of formula (I) being present in a weight concentration ranging from 0.001% to 10% with respect to a total weight of said composition.

15. The method of claim 9, wherein said compound of formula (I) is DL-alpha-tocopherol phosphate.

16. The method of claim 9, wherein said salt of compound of formula (I) is selected from a monosodium salt and a disodium salt.

17. A method for cosmetic care comprising topically delivering on body skin areas of a person a cosmetically effective amount of a cosmetically acceptable salt of a tocopherol phosphate, selected from the group consisting of:
a) an α-tocopherol compound of general formula (I), as follows:

(I)

[Structure of tocopherol phosphate compound]

wherein:
$R_1$ represents a hydrogen atom, an alkyl radical having from 1 to 4 carbon atoms, or an alpha-tocopheryl radical,
$R_2$ represents a hydrogen atom, an alkyl radical having from 1 to 4 carbon atoms, or $R_2O$ represents an oxyethylenated chain, of formula $$—(O—CH_2—\overset{R_4}{\underset{|}{CH}})_n—OR_3,$$

wherein
$R_3$ and $R_4$ represent independently a hydrogen atom or a methyl radical, and n represents an integer number greater than or equal to 1, and wherein
at least one of $R_1$ and $R_2$ is a hydrogen atom,
b) a DL form of said tocopherol-phosphate of formula
c) a D form of said tocopherol-phosphate of formula (I); and
d) a cosmetically acceptable ester of said tocopherol-phosphate of formula (I), wherein one of $R_1$ and $R_2$ is alkyl, alpha-tocopheryl or $R_2O$ represents said oxyethylenated chain, and the other of $R_1$ and $R_2$ is a hydrogen atom, said tocopherol compound being optionally admixed with a cosmetically acceptable excipient.

18. The method of claim 17, wherein said cosmetically acceptable salt of tocopherol phosphate is monosodium or disodium DL-alpha-tocopherol phosphate incorporated in a cosmetically acceptable excipient to constitute a composition wherein said monosodium or disodium salt of tocopherol phosphate is present in a weight concentration ranging from 0.001% to 10% with respect to a total weight of said composition.

19. A method of protection of skin cells from damage caused by free radicals comprising topically applying on body skin areas of a person an effective amount of a cosmetically acceptable salt of a tocopherol phosphate, selected from the group consisting of:
(a) an α-tocopherol compound of general formula (I), as follows:

(I)

[Structure of tocopherol phosphate compound]

wherein:
$R_1$ represents a hydrogen atom, an alkyl radical having from 1 to 4 carbon atoms, or an alpha-tocopheryl radical,
$R_2$ represents a hydrogen atom, an alkyl radical having from 1 to 4 carbon atoms, or $R_2O$ represents an oxyethylenated chain, of formula $$—(O—CH_2—\overset{R_4}{\underset{|}{CH}})_n—OR_3,$$

wherein
$R_3$ and $R_4$ represent independently a hydrogen atom or a methyl radical, and n represents an integer number greater than or equal to 1, and wherein
at least one of $R_1$ and $R_2$ is a hydrogen atom;
b) a DL form of said tocopherol-phosphate of formula
c) a D form of said tocopherol-phosphate of formula (I); and
d) a cosmetically acceptable ester of said tocopherol-phosphate of formula (I), wherein one of $R_1$ and $R_2$ is alkyl, alpha-tocopheryl or $R_2O$ represents said oxyethylenated chain, and the other of $R_1$ and $R_2$ is a hydrogen atom;

said tocopherol compound being optionally admixed with a cosmetically or pharmaceutically acceptable excipient.

20. The method of claim 19, wherein said cosmetically acceptable salt of tocopherol phosphate is monosodium or disodium DL-alpha-tocopherol phosphate incorporated in a cosmetically acceptable excipient to constitute a composition wherein said monosodium or disodium salt of tocopherol phosphate is present in a weight concentration ranging from 0.001% to 10% with respect to a total weight of said composition.

* * * * *